(12) United States Patent
Taldone et al.

(10) Patent No.: US 9,546,170 B2
(45) Date of Patent: Jan. 17, 2017

(54) HSP90 INHIBITORS

(75) Inventors: Tony Taldone, New York, NY (US); Gabriela Chiosis, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 14/110,095

(22) PCT Filed: Apr. 5, 2012

(86) PCT No.: PCT/US2012/032373
§ 371 (c)(1),
(2), (4) Date: Oct. 4, 2013

(87) PCT Pub. No.: WO2012/138896
PCT Pub. Date: Oct. 11, 2012

(65) Prior Publication Data
US 2014/0045867 A1    Feb. 13, 2014

Related U.S. Application Data

(60) Provisional application No. 61/472,061, filed on Apr. 5, 2011.

(51) Int. Cl.
*C07D 473/34* (2006.01)
*C07D 473/40* (2006.01)

(52) U.S. Cl.
CPC ........... *C07D 473/34* (2013.01); *C07D 473/40* (2013.01)

(58) Field of Classification Search
CPC .............................. C07D 473/34; A61K 31/52
See application file for complete search history.

(56) References Cited

U.S. PATENT DOCUMENTS

| | | | |
|---|---|---|---|
| 7,067,507 B2 * | 6/2006 | Pulley et al. | 514/183 |
| 7,834,181 B2 | 11/2010 | Chiosis et al. | |
| 8,703,942 B2 | 4/2014 | Chiosis et al. | |
| 2005/0004026 A1 | 1/2005 | Kasibhatla et al. | |
| 2005/0049263 A1 | 3/2005 | Kasibhatla et al. | |
| 2005/0107343 A1 | 5/2005 | Kasibhatla et al. | |
| 2005/0113339 A1 | 5/2005 | Kasibhatla et al. | |
| 2005/0113340 A1 | 5/2005 | Kasibhatla et al. | |
| 2005/0119292 A1 | 6/2005 | Gravestock et al. | |
| 2005/0256183 A1 | 11/2005 | Kasibhatla et al. | |
| 2008/0096903 A1 | 4/2008 | Chen et al. | |
| 2008/0234297 A1 | 9/2008 | Qian et al. | |
| 2008/0234314 A1 | 9/2008 | Cai et al. | |
| 2008/0253865 A1 | 10/2008 | Bailly et al. | |
| 2009/0298857 A1 | 12/2009 | Chiosis et al. | |
| 2012/0208806 A1 | 8/2012 | Chiosis et al. | |
| 2014/0088121 A1 | 3/2014 | Sun et al. | |
| 2014/0227183 A1 | 8/2014 | Chiosis et al. | |
| 2014/0378452 A1 | 12/2014 | Chiosis | |

FOREIGN PATENT DOCUMENTS

| | | |
|---|---|---|
| JP | 2009-521446 A | 6/2009 |
| JP | 2009-542716 A | 12/2009 |
| JP | 2010-507582 A | 3/2010 |
| JP | 2010-522184 A | 7/2010 |
| JP | 2013-507381 A | 3/2013 |
| WO | WO-98/51702 A1 | 11/1998 |
| WO | WO-00/61578 A1 | 10/2000 |
| WO | WO-02/36075 A2 | 5/2002 |
| WO | WO-2006/084030 A2 | 8/2006 |
| WO | WO-2007/075572 A2 | 7/2007 |
| WO | WO-2007/134298 A2 | 11/2007 |
| WO | WO-2008/005937 A2 | 1/2008 |
| WO | WO-2008/033747 A2 | 3/2008 |
| WO | WO-2008/049105 A2 | 4/2008 |
| WO | WO-2008/056120 A1 | 5/2008 |
| WO | WO-2008/115262 A2 | 9/2008 |

(Continued)

OTHER PUBLICATIONS

American Chemical Society (ACS). STN Chemical Abstract Service (CAS). CAS RN Database. (c) Oct. 2008.*
Young, A. "Four Decades of Neurodegenerative Disease Research: How Far We Have Come!" The Journal of Neuroscience. (Oct. 14, 2009), vol. 29(41), pp. 12722-12728.*
"List of Cancer Chemotherapy Drugs." © 2013. Available from: < https://www.navigatingcancer.com/library/all/chemotherapy_drugs >.*
Baade, P., et al. "One in four cancers preventable—but first we need the willpower." (c) 2013. Available from: < http://theconversation.com/one-in-four-cancers-preventable-but-first-we-need-the-willpower-5850 >.*

(Continued)

*Primary Examiner* — Andrew D Kosar
*Assistant Examiner* — John S Kenyon
(74) *Attorney, Agent, or Firm* — Choate, Hall & Stewart-LLP; John Rearick; Gang Wang

(57) ABSTRACT

The disclosure relates to Compounds of Formula (1):

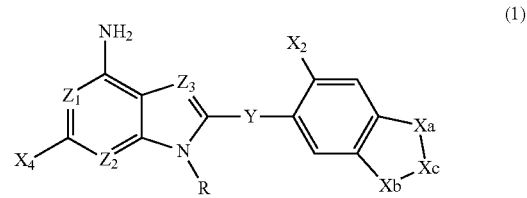

and pharmaceutically acceptable salts thereof wherein $Z_1$, $Z_2$, $Z_3$, Xa, Xb, Xc, Y, $X_2$, and $X_4$ are as defined herein, compositions comprising an effective amount of a Compound of Formula (1) or a pharmaceutically acceptable salt thereof, and methods to treat or prevent a condition, such as cancer which overexpresses Her-kinases, comprising administering to an patient in need thereof a therapeutically effective amount of a Compound of Formula (1) or a pharmaceutically acceptable salt thereof.

11 Claims, No Drawings

(56) References Cited

FOREIGN PATENT DOCUMENTS

| WO | WO 2008/115719 A1 | 9/2008 | | |
|---|---|---|---|---|
| WO | WO 2008115719 A1 | * | 9/2008 | ........... C07D 471/04 |
| WO | WO-2009/007399 A1 | 1/2009 | | |
| WO | WO-2009/042646 A1 | 4/2009 | | |
| WO | WO-2009065035 A1 | 5/2009 | | |
| WO | WO-2010/083403 A1 | 7/2010 | | |
| WO | WO-2011/044394 A1 | 4/2011 | | |
| WO | WO-2012/138894 A1 | 10/2012 | | |
| WO | WO-2012/138896 A1 | 10/2012 | | |

OTHER PUBLICATIONS

Kang, Y., et al. "Discovery and development of purine-scaffold Hsp90 inhibitors." Expert Opin. Drug Discov. (2008), vol. 3 (1), pp. 99-114.*

Medline Plus. "Degenerative Nerve Disease." (c) 2014. Available from: < http://www.nlm.nih.gov/medlineplus/degenerativenervediseases.html >.*

Chiosis, G. "Targeting chaperones in transformed systems—a focus on Hsp90 and cancer." Expert Opin. Ther. Targets. (2006), vol. 10(1), pp. 37-50.*

Mutyala, S. "Six Highly Treatable Cancers." DailyRx.com. (c) 2014. Available from: < http://www.dailyrx.com/some-cancers-have-high-survival-rates-early-detection >.*

American Chemical Society. STN Database. RN 1061319-57-0.*

He et al., Identification of Potent Water Soluble Purine-Scaffold Inhibitors of the Heat Shock Protein 90, Journal of Medicinal Chemistry, 49(1): 381-390 (2006).

International Search Report of PCT/US2012/032373, 4 pages (mailed Jun. 20, 2012).

Written Opinion of PCT/US2012/032373, 5 pages (mailed Jun. 20, 2012).

Written Opinion of PCT/US2012/032373, 5 pages (mailed Mar. 14, 2013).

International Preliminary Report on Patentability of PCT/US2012/032373, 5 pages (completed Jun. 19, 2013).

Breinig et al., Targeting Heat Shock Protein 90 with Non-Quinone Inhibitors: A Novel Chemotherapeutic Approach in Human Hepatocellular Carcinoma, Hepatology, 50(1): 102-112 (2009).

Caldas-Lopes et al., Hsp90 Inhibitor PU-H71, a Multimodal Inhibitor of Malignancy, Induces Complete Responses in Triple-Negative Breast Cancer Models., PNAS Early Edition, 1-6 (2009).

Cerchietti et al., A Purine Scaffold Hsp90 Inhibitor Destabilize BCL-6 and has Specific Antitumor Activity in BCL-6-Dependent B Cell Lymphomas, Nature Medicine, 15(12): 1369-1377 (2009).

Du et al., High-throughput Screening Fluorescence Polarization Assay for Tumor-Specific hsp90, J. Biomol. Screen, 12: 915-924 (2007).

Marubayashi et al., HSP90 is a Therapeutic Target in JAK2-dependent Myeloproliferative Neoplasms in Mice and Humans, The Journal of Clinical Investigation, 120(10): 3587-3593 (2010).

Dymock et al., Adenine derived inhibitors of the molecular chaperone HSP90-SAR explained Through Multiple X-Ray Structures, Bioorganic & Medicinal Chemistry Letters, 14(2): 325-328 (2004).

European Search Report for 12717520.6, 4 pages (dated Aug. 7, 2014).

International Search Report of PCT/US2012/032371, 6 pages (mailed Aug. 20, 2012).

Sgobba, M., et al., Structure-Based and in silico Design of Hsp90 Inhibitors, Chem. Med. Chem., 4(9): 1399-1409 (2009).

Written Opinion of PCT/US2012/032371, 10 pages (mailed Aug. 20, 2012).

Written Opinion of PCT/US2012/032371, 5 pages (mailed Mar. 12, 2013).

U.S. Appl. No. 13/176,903, Jul. 6, 2011, Chiosis.

* cited by examiner

HSP90 INHIBITORS

This application claims the benefit of and priority from U.S. provisional application no. 61/472,061, filed Apr. 5, 2011, the contents of which are incorporated herein by reference.

GOVERNMENT LICENSE RIGHTS

This invention was made with government support under grant number AG032969 awarded by National Institutes of Health. The government has certain rights in the invention.

1. BACKGROUND

This application relates to compounds that inhibit heat shock protein 90 (Hsp90).

The Hsp90 family of proteins has four recognized members in mammalian cells: Hsp90 α and β, Grp94 and Trap-1. Hsp90 α and β exist in the cytosol and the nucleus in association with a number of other proteins. Hsp90 in its various forms is the most abundant cellular chaperone, and has been shown in experimental systems to be required for ATP-dependent refolding of denatured or "unfolded" proteins. It has therefore been proposed to function as part of the cellular defense against stress. When cells are exposed to heat or other environmental stresses, the aggregation of unfolded proteins is prevented by pathways that catalyze their refolding or degradation. This process depends on the association of the unfolded protein in an ordered fashion with multiple chaperones (Hsp60, Hsp90, Hsp70 and p23), forming a "refoldosome" and ultimately the ATP-dependent release of the chaperones from the refolded protein.

Hsp90 can also play a role in maintaining the stability and function of mutated proteins. It seems to be required for expression of mutated p53 and v-src to a much greater extent than for their wild-type counterparts. It has been suggested that this occurs as a result of Hsp90-mediated suppression of the phenotypes of mutations that lead to protein unfolding.

Hsp90 is also necessary to the conformational maturation of several key proteins involved in the growth response of the cell to extracellular factors. These include the steroid receptors as well as certain kinases (i.e., Raf serine kinase, v-src and Her2). The mechanism whereby Hsp90 affects these proteins is not fully understood, but appears to be similar to its role in protein refolding. In the case of the progesterone receptor, it has been shown that binding and release of Hsp90 from the receptor occurs in a cyclic fashion in concert with release of other chaperones and immunophilins and is required for high affinity binding of the steroid to the receptor. Thus, Hsp90 could function as a physiologic regulator of signaling pathways, even in the absence of stress.

Hsp90 has been shown to be overexpressed in multiple tumor types and as a function of oncogenic transformation. Whether it plays a necessary role in maintaining transformation is unknown, but it could have at least three functions in this regard. Cancer cells grow in an environment of hypoxia, low pH and low nutrient concentration. They also rapidly adapt to or are selected to become resistant to radiation and cytotoxic chemotherapeutic agents. Thus, the general role of Hsp90 in maintaining the stability of proteins under stress may be necessary for cell viability under these conditions. Secondly, cancer cells harbor mutated oncogenic proteins. Some of these are gain-of-function mutations which are necessary for the transformed phenotype. Hsp90 may be required for maintaining the folded, functionally-active conformation of these proteins. Thirdly, activation of signaling pathways mediated by steroid receptors, Raf and other Hsp90 targets is necessary for the growth and survival of many tumors which thus probably also require functional Hsp90.

Hsp90 has been recognized as a viable target for therapeutic agents. Hsp90 family members possess a unique pocket in their N-terminal region that is specific to and conserved among all Hsp90s from bacteria to mammals, but which is not present in other molecular chaperones. The endogenous ligand for this pocket is not known, but it binds ATP and ADP with low affinity and has weak ATPase activity. The ansamycin antibiotics geldanamycin (GM) and herbimycin (HA) have been shown to bind to this conserved pocket, and this binding affinity has been shown for all members of the Hsp90 family. International Patent Publication No. WO98/51702 discloses the use of ansamycin antibiotics coupled to a targeting moiety to provide targeted delivery of the ansamycin leading to the degradation of proteins in and death of the targeted cells. International Patent Publication No. WO00/61578 relates to bifunctional molecules having two moieties which interact with the chaperone protein Hsp90, including in particular homo- and heterodimers of ansamycin antibiotics. These bifunctional molecules act to promote degradation and/or inhibition of HER-family tyrosine kinases and are effective for treatment of cancers which overexpress Her-kinases.

Exemplary small molecule therapeutics that bind to the same binding pocket of Hsp90 as ATP and the ansamycin antibiotics are disclosed in PCT Publication Nos. WO02/36075, WO2006/084030, WO2009/042646, WO2009/065035, and WO2011/044394; U.S. Pat. No. 7,834,181; and U.S. Patent Publication Nos. 2005/0113339, 2005/0004026, 2005/0049263, 2005/0256183, 2005/0119292, 2005/0113340, 2005/0107343, 2008/0096903, 2008/0234297, 2008/0234314, 2008/0253865, and 2009/0298857, all of which are incorporated herein by reference.

In particular, certain small molecule therapeutics that bind to the same binding pocket of Hsp90 can be described by the following general structural formula where $Z_1$, $Z_2$, and $Z_3$ are selected from CH and N:

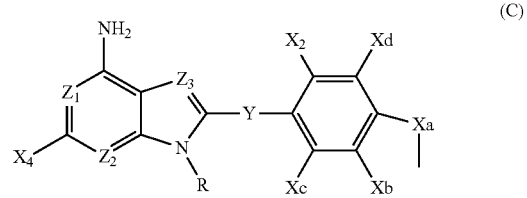

(C)

While these compounds can be active as inhibitors of Hsp90, their level of activity is extremely variable with measured values for $EC_{50}$ and $IC_{50}$ being reported in anywhere from the micromolar to nanomolar ranges.

2. SUMMARY

In one aspect of the disclosure, new compounds that inhibit Hsp90 are described.

A compound of Formula (1):

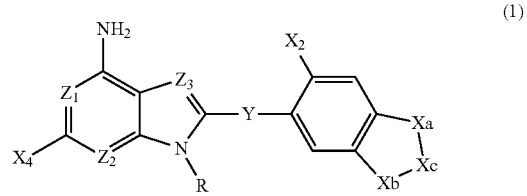

(1)

or a pharmaceutically acceptable salt thereof, wherein:
(a) each of $Z_1$, $Z_2$ and $Z_3$ is independently CH or N;
(b) Y is S;
(c) Xa and Xb are O;
(d) Xc is —$CH_2$—;
(e) $X_2$ is —$NR_1R_2$, wherein $R_1$ and $R_2$ are each independently H, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl;
(f) $X_4$ is hydrogen or halogen; and
(g) R is $R_{10}$—NH—$R_{11}$ wherein $R_{10}$ is ethylene or propylene, and $R_{11}$ is a branched alkyl.

The compounds are useful in pharmaceutical compositions for the treatment of cancer and neurodegenerativer diseases through their activity as Hsp90 inhibitors and can be used in a method of treating cancer or neurodegenerative diseases.

3. DETAILED DESCRIPTION

The invention includes the following:
(1) A Compound of Formula (1):

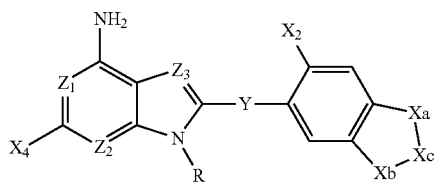

(1)

or a pharmaceutically acceptable salt thereof, wherein:
(a) each of $Z_1$, $Z_2$ and $Z_3$ is independently CH or N;
(b) Y is S;
(c) Xa and Xb are O;
(d) X is —$CH_2$—;
(e) $X_2$ is —$NR_1R_2$, wherein $R_1$ and $R_2$ are each independently H, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl, or a protonated form thereof;
(f) $X_4$ is hydrogen or halogen; and
(g) R is —$R_{10}$—NH—$R_{11}$ wherein $R_{10}$ is ethylene or propylene, and $R_{11}$ is a branched alkyl.

(2) Compounds of (1) in which $Z_1$, $Z_2$ and $Z_3$ are all N as shown in formula (2)

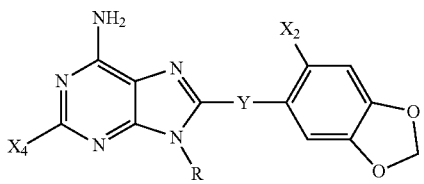

(2)

or a pharmaceutically acceptable salt thereof,
(3) Compounds of (1) or (2) or a pharmaceutically acceptable salt thereof in which $R_{11}$ is neopentyl, isopropyl or t-butyl.
(4) Compounds of one of the above (1) to (3) or a pharmaceutically acceptable salt thereof in which $X_2$ is dimethylamine.

(5) A pharmaceutical composition comprising the compound as in one of the above (1) to (5) or a pharmaceutically acceptable salt thereof and a pharmaceutically acceptable carrier.
(6) A method for treating or preventing cancer or a neurodegenerative disorder, comprising administering to a patient in need thereof a therapeutically effective amount of a compound as in one of the above (1) to (5) or a pharmaceutically acceptable salt thereof.
(7) Use of a compound as in one of the above (1) to (5) or a pharmaceutically acceptable salt thereof in formulating a pharmaceutical composition for the treatment or prevention of cancer or a neurodegenerative disorder.
(8) A method for the inhibition of Hsp90, comprising contacting Hsp90 with an Hsp90 function inhibiting amount of a compound as in one of the above (1) to (5) or a pharmaceutically acceptable salt thereof.
(9) Use of a compound as in one of the above (1) to (5) or a pharmaceutically acceptable salt thereof in formulating a pharmaceutical composition for the inhibition of Hsp90.

As stated above, the disclosure encompasses Compounds of Formula (1):

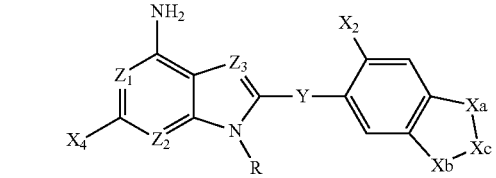

(1)

or a pharmaceutically acceptable salt thereof, wherein:
(a) each of $Z_1$, $Z_2$ and $Z_3$ is independently CH or N;
(b) Y is S;
(c) Xa and Xb are O;
(d) Xc is —$CH_2$—
(e) $X_2$ is —$NR_1R_2$, wherein $R_1$ and $R_2$ are each independently H, $C_1$-$C_6$ alkyl, $C_2$-$C_6$ alkenyl, $C_2$-$C_6$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl, or a protonated form thereof;
(f) $X_4$ is hydrogen or halogen; and
(g) R is —$R_{10}$—NH—$R_{11}$ wherein $R_{10}$ is ethylene or propylene, and $R_{11}$ is a branched alkyl.

Definitions

As used in connection with the present disclosure, the terms used herein have the following meaning:

The terms "alkyl" and "substituted alkyl" are interchangeable unless otherwise specifically noted and refer to substituted and unsubstituted $C_1$-$C_{10}$ straight-chain saturated aliphatic hydrocarbon groups, i.e., groups having 1, 2, 3, 4, 5, 6, 7, 8, 9, or 10 carbon atoms, and substituted and unsubstituted $C_3$-$C_{10}$ branched saturated aliphatic hydrocarbon groups, i.e., groups having 3, 4, 5, 6, 7, 8, 9, or 10 carbon atoms. For example, "alkyl" includes but is not limited to: methyl (Me), ethyl (Et), propyl (Pr), isopropyl, butyl (Bu), tert-butyl, pentyl, hexyl, heptyl, octyl, nonyl, decyl, and the like. In one embodiment, an alkyl is a $C_1$-$C_6$ alkyl, i.e., a group having 1, 2, 3, 4, 5, or 6 carbon atoms. An alkyl can be substituted with 1, 2, or 3 substituents or optionally substituted with 1, 2, or 3 substituents. Illustrative examples of substituted $C_1$-$C_6$ alkyl groups include —$CH_2OH$, —$CF_2OH$, —$CH_2C(CH_3)_2C(O)OCH_3$, —$CF_3$, —$C(O)CF_3$, —$C(O)CH_3$, —$(CH_2)_4SCH_3$, —$CH(C(O)OH)CH_2CH_2C$ (O)N(CH$_3$)$_2$, —(CH$_2$)$_5$NHC(O)NH$_2$, —CH$_2$CH$_2$-(4-fluorophenyl), —CH(OCH$_3$)CH$_2$CH$_3$, —CH$_2$SO$_2$NH$_2$, and —CH(CH$_3$)CH$_2$CH$_2$OC(O)CH$_3$. The term "branched alkyl" encompasses alkyl groups that are linear alkyl groups attached through a non-terminal carbon atom as well as alkyl groups that include a defined branch point. Illustrative examples of branched alkyl groups thus include isopropyl, isobutyl, sec-butyl, t-butyl, isopentyl, sec-pentyl, t-pentyl, and neopentyl groups. The terms "alkenyl" and "substituted alkenyl" are interchangeable unless otherwise specifically noted and refer to substituted and unsubstituted C$_2$-C$_{10}$ straight-chain aliphatic hydrocarbon groups having 1, 2, or 3 carbon-carbon double bonds, i.e., groups having 1, 2, 3, 4, 5, 6, 7, 8, 9, or 10 carbon atoms, and substituted and unsubstituted C$_3$-C$_{10}$ branched aliphatic hydrocarbon groups having 1, 2, or 3 carbon-carbon double bonds, i.e., groups having 3, 4, 5, 6, 7, 8, 9, or 10 carbon atoms. For example, "alkenyl" includes but is not limited to: ethenyl, 1-prop-1-enyl, 1-prop-2-enyl, 2-prop-1-enyl, 1-but-3-enyl, 2-pent-2-enyl, 1-hex-6-enyl, 1-hept-7-enyl, 1-oct-8-enyl, and the like. In one embodiment, an alkenyl is a C$_2$-C$_6$ alkenyl, i.e., a group having 2, 3, 4, 5, or 6 carbon atoms and 1 or 2 carbon-carbon double bonds. An alkenyl can be substituted with 1, 2, or 3 substituents or optionally substituted with 1, 2, or 3 substituents. Illustrative examples of substituted C$_2$-C$_6$ alkenyl groups include —C(H)═CHCH$_2$OH, —C(H)═CF$_2$, —CH$_2$C(H)═CH(CH$_2$)$_2$CF$_2$OH, —CH$_2$C(═CH$_2$)C(O)OCH$_3$, —C(H)═CHCF$_3$, —CH$_2$CH$_2$C(H)═CHC(O)CH$_3$, —C(H)═C(CH$_3$)SCH$_3$, —C(H)═CHC(H)═C(CH$_3$)C(O)OCH$_3$, and —C(H)═C═CHOC(O)CH$_3$.

The terms "alkynyl" and "substituted alkynyl" are interchangeable unless otherwise specifically noted and refer to substituted and unsubstituted C$_2$-C$_{10}$ straight-chain aliphatic hydrocarbon groups having 1, 2, or 3 carbon-carbon triple bonds, i.e., groups having 1, 2, 3, 4, 5, 6, 7, 8, 9, or 10 carbon atoms, and substituted and unsubstituted C$_3$-C$_{10}$ branched aliphatic hydrocarbon groups having 1, 2, or 3 carbon-carbon triple bonds, i.e., groups having 3, 4, 5, 6, 7, 8, 9, or 10 carbon atoms. For example, "alkynyl" includes but is not limited to: ethynyl, 1-prop-1-ynyl, 1-prop-2-ynyl, 2-prop-1-ynyl, 3-prop-1-ynyl, 1-but-3-ynyl, 2-pent-2-ynyl, 1-hex-6-ynyl, 1-hept-7-ynyl, 1-oct-8ynyl, and the like. In one embodiment, an alkynyl is a C$_2$-C$_6$ alkynyl, i.e., a group having 2, 3, 4, 5, or 6 carbon atoms and 1 or 2 carbon-carbon triple bonds. An alkynyl can be substituted with 1, 2, or 3 substituents or optionally substituted with 1, 2, or 3 substituents. Illustrative examples of substituted C$_2$-C$_6$ alkynyl groups include —C≡CCH$_2$OH, —C≡CF, —CH$_2$C≡C(CH$_2$)$_2$CF$_2$OH, —C≡CCH$_2$C(O)OCH$_3$, —CH$_2$C≡CCF$_3$, —CH$_2$CH$_2$C≡CC(O)CH$_3$, —C≡CSCH$_3$, and —C≡CC(O)OC(O)CH$_3$.

The terms "cycloalkyl" and "substituted cycloalkyl" are interchangeable unless otherwise specifically noted and refer to a mono- or multi-ringed carbocycle wherein each ring contains 3, 4, 5, 6, 7, 8, 9, or 10 carbon atoms, and wherein any ring can contain 1, 2, or 3 carbon-carbon double or triple bonds. For example, "cycloalkyl" includes but is not limited to: cyclopropyl, cyclobutyl, cyclopentyl, cyclohexyl, cycloalkenyl, cycloalkynyl, and cycloheptyl. A cycloalkyl can be substituted with 1, 2, or 3 substituents or optionally substituted with 1, 2, or 3 substituents.

The terms "aryl" and "substituted aryl" are interchangeable unless otherwise specifically noted and refer to a monocyclic, polycyclic, biaryl aromatic groups covalently attached at any ring position capable of forming a stable covalent bond, certain preferred points of attachment being apparent to those in the art (e.g., 3-phenyl, 4-naphthyl, and the like). An aryl can be substituted with 1, 2, or 3 substituents or optionally substituted with 1, 2, or 3 substituents. The definition of "aryl" includes but is not limited to heteroaryl. Illustrative examples of aryl groups include phenyl, biphenyl, naphthyl, dihydronaphthyl, tetrahydronaphthyl, indenyl, indanyl, azulenyl, anthryl, phenanthryl, fluorenyl, pyrenyl, anthracenyl, pyridyl, pyrimidyl, pyridizinyl, thiadiazolyl, and the like.

The term "heteroalkyl" refers to an alkyl group where one or more of the carbon atoms or hydrogen atoms present is replaced, independently, with a nitrogen, oxygen, sulfur, or halogen heteroatom. If the heteroatom does not have the same number of valence sites as the carbon atom it replaces, the number of hydrogens bonded to the replacement heteroatom may need to be increased or decreased to match the number of valence sites of the heteroatom. For example, if a carbon atom (with a valence of four) is replaced by a nitrogen atom (valence of three), one of the hydrogen atoms formerly attached to the replaced carbon is deleted. Likewise, if a carbon atom is replaced by a halogen atom (valence of one), three of the hydrogen atoms formerly attached to the replaced carbon is deleted. The term "heteroalkyl" also refers to (1) an alkyl group where at least one of the hydrogen atoms attached to a carbon or (2) to a heteroalkyl group where at least one of the hydrogen atoms attached to a heteroatom of the heteroalkyl can be substituted with at least one of the following: alkyl, aryl, and heteroalkyl.

The terms "heteroaryl" and "substituted heteroaryl" are interchangeable unless otherwise specifically noted and the terms "heterocyclo" and "substituted heterocyclo" are interchangeable unless otherwise specifically noted and these terms refer to a monovalent unsaturated group having a single ring or multiple condensed rings, from 1 to 8 carbon atoms, and from 1 to 4 heteroatoms within the ring, each heteroatom being independently selected from nitrogen, sulfur, or oxygen. In either heteroaryl or heterocyclo, the point of attachment to the molecule can be at a heteroatom or elsewhere within the ring. A heteroaryl or heterocyclo can be substituted with 1, 2, or 3 substituents or optionally substituted with 1, 2, or 3 substituents.

Illustrative examples of heteroaryl groups include thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrol-3-yl, pyrrol-1-yl, indolyl, isoindolyl, 3H-indolyl, indolinyl, indolizinyl, indazolyl, imidazolyl, imidazol-4-yl, 2H-imidazolinyl, benzimidazolyl, pyridyl, pyrazinyl, pyradazinyl, pyrimidinyl, pyrimidin-2-yl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, pyrazol-3-yl, triazolyl, 1,2,4-triazol-1-yl, tetrazolyl, tetrazol-1-yl, thiazolyl, thiazol-4-yl, isothiazolyl, benzthiazolyl, oxazolyl, oxazol-2-yl, isoxazolyl, isoxazol-3-yl, benzoxazolyl, oxadiazolyl, 1,2,4-oxadiazol-3-yl, thiadiazolyl, pyridazin-4-yl, pyrazin-2-yl, thiophen-2-yl, furan-2-yl, pyridin-2-yl, pyridin-4-yl, pyrimidin-2-yl, and the like.

When any group is substituted with 1, 2, or 3 substituents or optionally substituted with 1, 2, or 3 substituents, each substituent is independently selected from the group comprising halo, —OH, —SH, —CN, —NO$_2$, —NH$_2$, trihalomethyl, pentahaloethyl, C$_1$-C$_{10}$alkyl, arylC$_0$-C$_{10}$alkyl, C$_0$-C$_{10}$alkyloxyC$_0$-C$_{10}$alkyl, arylC$_0$-C$_{10}$alkyloxyC$_0$-C$_{10}$alkyl, C$_0$-C$_{10}$alkylthioC$_0$-C$_{10}$alkyl, arylC$_0$-

$C_{10}$alkylthio$C_0$-$C_{10}$alkyl, $C_0$-$C_{10}$alkylamino$C_0$-$C_{10}$alkyl, aryl$C_0$-$C_{10}$alkylamino$C_0$-$C_{10}$alkyl, N-aryl-N-$C_0$-$C_{10}$alkylamino$C_0$-$C_{10}$alkyl, $C_1$-$C_{10}$alkylcarbonyl$C_0$-$C_{10}$alkyl, aryl$C_1$-$C_{10}$alkylcarbonyl$C_0$-$C_{10}$alkyl, $C_1$-$C_{10}$alkylcarboxy$C_0$-$C_{10}$alkyl, aryl$C_1$-$C_{10}$alkylcarboxy$C_0$-$C_{10}$alkyl, $C_1$-$C_{10}$alkylcarbonylamino$C_0$-$C_{10}$alkyl, aryl$C_1$-$C_{10}$alkylcarbonylamino$C_0$-$C_{10}$alkyl, -$C_0$-$C_{10}$alkylC(O)OR$_X$, and —$C_0$-$C_{10}$alkylC(O)NR$_Y$R$_Z$ wherein R$_X$, R$_Y$ and R$_Z$ are independently selected from hydrogen, alkyl, and aryl or R$_Y$ and R$_Z$ are taken together with the nitrogen to which they are attached to form in a saturated cyclic or unsaturated cyclic system having 3, 4, 5, 6, 7, or 8 carbon atoms with at least one substituent as defined above. A "$C_0$alkyl," as in $C_0$-$C_{10}$alkyl, is a covalent bond.

The term "$C_0$-$C_{10}$alkyloxy" refers to an alkyl group having the indicated number of carbon atoms and attached to the molecule through an oxygen atom. In one embodiment, a $C_0$-$C_{10}$alkyloxy is a $C_1$-$C_6$alkyloxy, i.e., a group having 1, 2, 3, 4, 5, or 6 carbon atoms. Illustrative examples of alkyloxy groups include methoxy, ethoxy, n-propyloxy, and isopropyloxy. Thus, the term "$C_0$-$C_{10}$alkyloxy$C_0$-$C_{10}$alkyl" refers to a $C_0$-$C_{10}$alkyloxy attached through an oxygen atom to a $C_0$-$C_{10}$alkyl which is attached to the molecule. Likewise, the term "aryl$C_0$-$C_{10}$alkyloxy$C_0$-$C_{10}$alkyl" refers to a $C_0$-$C_{10}$alkyloxy, which is substituted by aryl, attached through an oxygen atom to a $C_0$-$C_{10}$alkyl which is attached to the molecule. A "$C_0$alkyloxy" is —OH.

The term "$C_0$-$C_{10}$alkylthio" refers to an alkyl group having the indicated number of carbon atoms and attached to the molecule through a sulfur atom. In one embodiment, a $C_0$-$C_{10}$alkylthio is a $C_1$-$C_6$alkylthio, i.e., a group having 1, 2, 3, 4, 5, or 6 carbon atoms. Illustrative examples of alkyloxy groups include methylthio, ethylthio, n-propylthio, and isopropylthio. Thus, the term "$C_0$-$C_{10}$alkylthio$C_0$-$C_{10}$alkyl" refers to a $C_0$-$C_{10}$alkylthio attached through a sulfur atom to a $C_0$-$C_{10}$alkyl which is attached to the molecule. Likewise, the term "aryl$C_0$-$C_{10}$alkylthio$C_0$-$C_{10}$alkyl" refers to a $C_0$-$C_{10}$alkylthio, which is substituted by aryl, attached through a sulfur atom to a $C_0$-$C_{10}$alkyl which is attached to the molecule. A "$C_0$alkylthio" is —SH.

The term "$C_1$-$C_{10}$alkylcarbonyl" refers to an alkyl group having the indicated number of carbon atoms and attached to the molecule through the carbon atom of a carbonyl group. In one embodiment, a $C_1$-$C_{10}$alkylcarbonyl is a $C_1$-$C_6$alkylcarbonyl, i.e., a group having 1, 2, 3, 4, 5, or 6 carbon atoms, including the carbonyl carbon atom. Thus, the term "$C_1$-$C_{10}$alkylcarbonyl$C_0$-$C_{10}$alkyl" refers to a $C_1$-$C_{10}$alkylcarbonyl attached through the carbon atom of a carbonyl group to a $C_0$-$C_{10}$alkyl which is attached to the molecule. Likewise, the term "aryl$C_1$-$C_{10}$alkylcarbonyl$C_0$-$C_{10}$alkyl" refers to a $C_1$-$C_{10}$alkylcarbonyl, which is substituted by aryl, attached through the carbon atom of a carbonyl group to a $C_0$-$C_{10}$alkyl which is attached to the molecule.

The term "$C_1$-$C_{10}$alkylcarboxy" refers to an alkyl group having the indicated number of carbon atoms, including the carboxy's carbon atom, and attached to the molecule through the carboxy group, wherein the carboxy group has either a —C(=O)—O— or a —O—C(=O)— orientation. In one embodiment, a $C_1$-$C_{10}$alkylcarboxy is a $C_1$-$C_6$alkylcarboxy, i.e., a group having 2, 3, 4, 5, or 6 carbon atoms, including the carboxy's carbon atom. Thus, the term "$C_1$-$C_{10}$alkylcarboxy$C_0$-$C_{10}$alkyl" refers to a $C_1$-$C_{10}$alkylcarboxy attached through the carboxy group to a $C_0$-$C_{10}$alkyl which is attached to the molecule. Likewise, the term "aryl$C_1$-$C_{10}$alkylcarboxy$C_0$-$C_{10}$alkyl" refers to a $C_1$-$C_{10}$alkylcarboxy, which is substituted by aryl, attached through the carboxy group to a $C_0$-$C_{10}$alkyl which is attached to the molecule.

The term "$C_0$-$C_{10}$alkylamino" refers to an alkyl group having the indicated number of carbon atoms and attached to the molecule through the nitrogen atom of the amino group —N(R$_W$)—, wherein R$_W$ is H, $C_1$-$C_6$alkyl, or aryl. A "$C_0$alkylamino" is —NHR$_W$. In one embodiment, a $C_0$-$C_{10}$alkylamino is a $C_1$-$C_6$alkylamino, i.e., a group having 1, 2, 3, 4, 5, or 6 carbon atoms in the alkyl group and 0, 1, 2, 3, 4, 5, or 6 carbon atoms in the R$_W$ group. Thus, the term "$C_0$-$C_{10}$alkylamino$C_0$-$C_{10}$alkyl" refers to a $C_0$-$C_{10}$alkylamino attached through the nitrogen atom of an amino group to a $C_0$-$C_{10}$alkyl which is attached to the molecule. Likewise, the term "aryl$C_0$-$C_{10}$alkylamino$C_0$-$C_{10}$alkyl" refers to a $C_0$-$C_{10}$alkylamino, which is substituted by aryl, attached through the nitrogen atom of an amino group to a $C_0$-$C_{10}$alkyl which is attached to the molecule. The term "N-aryl-N—$C_0$-$C_{10}$alkylamino$C_0$-$C_{10}$alkyl" refers to an amine nitrogen atom substituted by aryl and $C_0$-$C_{10}$alkyl, that nitrogen atom being further attached to a $C_0$-$C_{10}$ alkyl which is attached to the molecule.

The term "$C_1$-$C_{10}$alkylcarbonylamino" refers to an alkyl group having the indicated number of carbon atoms, including the carbonylamino's (i.e., amide's) carbon atom, and attached to the molecule through the amide, group, wherein the amide group has either a —C(=O)N(R$_V$)— or a —N(R$_V$)C(=O)— orientation and wherein R$_V$ is H or $C_1$-$C_6$alkyl. In one embodiment, a $C_1$-$C_{10}$alkylcarbonylamino is a $C_1$-$C_6$alkylcarbonylamino, i.e., a group having 2, 3, 4, 5, or 6 carbon atoms, including the amide's carbon atom, in the alkyl group and 0, 1, 2, 3, 4, 5, or 6 carbon atoms in the R$_V$ group. Thus, the term "$C_1$-$C_{10}$alkylcarbonylamino$C_0$-$C_{10}$alkyl" refers to a $C_1$-$C_{10}$alkylcarbonylamino attached through the amide group to a $C_0$-$C_{10}$alkyl which is attached to the molecule. Likewise, the term "aryl$C_1$-$C_{10}$alkylcarbonylamino$C_0$-$C_{10}$alkyl" refers to a $C_1$-$C_{10}$alkylcarbonylamino, which is substituted by aryl, attached through the amide group to a $C_0$-$C_{10}$alkyl which is attached to the molecule.

The term "alkylaryl" refers to an aryl group as defined above that is substituted with 1, 2, or 3 alkyl groups as defined above; a tolyl group is an exemplary alkylaryl. In one embodiment, an alkylaryl group is a "lower alkylaryl" group having 1, 2, or 3 alkyl groups attached to an aryl group, each alkyl group having, independently, 1, 2, 3, 4, 5, or 6 carbon atoms.

The term "arylalkyl" refers to an alkyl group as defined above that is substituted with 1, 2, or 3 aryl groups as defined above; a benzyl group is an exemplary arylalkyl. In one embodiment, an arylalkyl group is a "lower arylalkyl" group having 1, 2, or 3 aryl groups attached to an alkyl group having 1, 2, 3, 4, 5, or 6 carbon atoms.

The term "heterocycloalkyl" refers to an alkyl group as defined above that is substituted with 1, 2, or 3 heterocyclo groups as defined above. In one embodiment, a heterocycloalkyl group is a "lower heterocycloalkyl" group having 1, 2, or 3 heterocyclo groups attached to an alkyl group having 1, 2, 3, 4, 5, or 6 carbon atoms.

The term "alkylheteroaryl" refers to a heteroaryl group as defined above that is substituted with 1, 2, or 3 alkyl groups as defined above. In one embodiment, a alkylheteroaryl group is a "lower alkylheteroaryl" group having 1, 2, or 3 alkyl groups attached to a heteroaryl group, each alkyl group having, independently, 1, 2, 3, 4, 5, or 6 carbon atoms.

The term "heteroarylalkyl" refers to an alkyl group as defined above that is substituted with 1, 2, or 3 heteroaryl groups as defined above. In one embodiment, a heteroarylalkyl group is a "lower heteroarylalkyl" group having 1, 2, or 3 heteroaryl groups attached to an alkyl group having 1, 2, 3, 4, 5, or 6 carbon atoms.

The term "alkylheteroarylalkyl" refers to a heteroarylalkyl group as defined above that is substituted with 1, 2, or 3 alkyl groups as defined above. In one embodiment, an alkylheteroarylalkyl group is a "lower alkylheteroarylalkyl" group with each alkyl portion having, independently, 1, 2, 3, 4, 5, or 6 carbon atoms.

The terms "halogen" and "halo" refer to fluorine, chlorine, bromine, and iodine.

Should there be doubt as to the agreement of a depicted chemical structure and a chemical name, the depicted chemical structure governs.

The term "pharmaceutically acceptable salt" refers to those salts which retain the biological effectiveness and properties of the "free" compounds of Formula (1). A pharmaceutically acceptable salt can be obtained from the reaction of the free base of a Compound of Formula (1) with an inorganic acid, for example, hydrochloric acid, hydrobromic acid, sulfuric acid, nitric acid, phosphoric acid, and the like, or an organic acid, for example, sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g., (+)-tartaric acid or (−)-tartaric acid or mixtures thereof), and the like. Certain compounds of Formula (1) have acidic substituents and can exist as pharmaceutically acceptable salts with pharmaceutically acceptable bases. The present disclosure includes such salts. Examples of such salts include metal counterion salts, such as sodium, potassium, lithium, magnesium, calcium, iron, copper, zinc, tin, silver, or aluminum salts, and organic amine salts, such as methylamine, dimethylamine, trimethylamine, diethylamine, triethylamine, n-propylamine, 2-propylamine, or dimethylisopropylamine salts, and the like. The term "pharmaceutically acceptable salt" includes mono-salts and compounds in which a plurality of salts is present, e.g., di-salts and/or tri-salts. Pharmaceutically acceptable salts can be prepared by methods known to those in the art.

Certain compounds of Formula (1) and/or their pharmaceutically acceptable salts can exist in more than one crystal form and the present disclosure encompasses each crystal form and mixtures thereof. These crystal forms can be prepared by methods known to those in the art.

The term "solvate" refers to a complex or aggregate formed by one or more molecules of a solute, e.g., a Compound of Formula (1) or its pharmaceutically acceptable salt, and one or more molecules of a solvent, which is present in stoichiometric or non-stoichiometric amount. Suitable solvents include but are not limited to water, acetic acid, ethanol, methanol, isopropanol, and n-propanol. Where the solvent is water, the solvate is a hydrate. Exemplary hydrates include but are not limited to a hemihydrate, a monohydrate, a dihydrate, a trihydrate, and a tetrahydrate. In one embodiment, the solvent is pharmaceutically acceptable. In another embodiment, the complex or aggregate is in a crystalline form. In another embodiment, the complex or aggregate is in a noncrystalline form. The present disclosure encompasses each solvate and mixtures thereof. These solvates can be prepared by methods known to those in the art.

Certain compounds of Formula (1) may exist in different tautomeric forms or as different geometric isomers, and the present disclosure includes each tautomer and/or geometric isomer of compounds of Formula (1) and mixtures thereof.

Certain compounds of Formula (1) may contain one or more chiral centers and exist in different optically active forms, and the present disclosure includes each optically active form of compounds of Formula (1) and mixtures thereof. When compounds of Formula (1) contain one chiral center, the compounds exist in two enantiomeric forms and the present disclosure includes both enantiomers and mixtures of enantiomers, such as racemic mixtures. The enantiomers may be resolved by methods known to the art, for example, by formation of diastereoisomeric salts which may be separated, e.g., by crystallization or liquid chromatography. Alternatively, specific enantiomers may be synthesized by asymmetric synthesis using optically active reagents, substrates, catalysts or solvents, or by converting one enantiomer into the other by asymmetric transformation. When a Compound of Formula (1) contains more than one chiral center, it may exist in diastereoisomeric forms. The diastereoisomeric compounds may be separated by methods known to the art, for example, by chromatography or crystallization, and the individual enantiomers may be separated as described above. The present disclosure includes each diastereoisomer of compounds of Formula (1) and mixtures thereof.

The term "isotopically enriched" refers to a Compound of Formula (1) that contains an unnatural proportion of an isotope at one or more of the atoms constituting the compound, and the present disclosure includes each isotopically enriched form of compounds of Formula (1) and mixtures thereof. In certain embodiments, an isotopically enriched compound contains unnatural proportions of one or more isotopes, including but not limited to hydrogen ($^1H$), deuterium ($^2H$), tritium ($^3H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 I) iodine-127 ($^{127}I$), iodine-129 ($^{129}I$), and iodine-131 ($^{131}I$). In another embodiment, an isotopically enriched compound contains unnatural proportions of one or more isotopes, including but not limited to $^1H$, $^2H$, $^{12}C$, $^{13}C$, $^{14}N$, $^{15}N$, $^{16}O$, $^{17}O$, $^{18}O$, $^{17}F$, $^{32}S$, $^{33}S$, $^{34}S$, $^{36}S$, $^{35}Cl$, $^{37}Cl$, $^{79}Br$, $^{81}Br$, and $^{127}I$. In another embodiment, an isotopically enriched compound is radioactive. In another embodiment, an isotopically enriched compound contains unnatural proportions of one or more isotopes, including but not limited to $^3H$, $^{11}C$, $^4C$, $^{13}N$, $^{14}O$, $^{15}O$, $^{18}F$, $^{35}S$, $^{36}Cl$, $^{123}I$, $^{125}I$, $^{129}I$, and $^{131}I$. In another embodiment, an isotopically enriched compound contains unnatural proportions of 123I, $^{124}I$, or $^{131}I$ and another isotope selected from $^3H$, $^{11}C$, $^{13}N$, $^{14}O$, $^{15}O$, $^{18}F$, $^{35}S$, and $^{36}Cl$. In another embodiment, an isotopically enriched compound contains an unnatural proportion of $^{123}I$, $^{124}I$, and/or $^{131}I$. In another embodiment, an isotopically enriched compound contains an unnatural proportion of $^{123}I$. In another embodiment, an isotopically enriched compound contains an unnatural proportion of $^{124}I$. In another embodiment, an isotopically enriched compound contains an unnatural proportion of $^{131}I$.

The term "isotopically enriched" refers to the percentage of incorporation of a less prevalent isotope (e.g., deuterium for hydrogen) of an element at a given location in a molecule in place of a more prevalent isotope (e.g., $^1H$ for hydrogen) of that element. When an atom at a particular location in a molecule is designated as a particular less prevalent isotope, it is understood that the abundance of that isotope at that location is substantially greater than its natural abundance.

The term "therapeutically effective amount" refers to an amount of a Compound of Formula (1) or a combination of two or more such compounds that inhibits, totally or partially, the progression of the treated condition or alleviates, at least partially, one or more symptoms of the condition. A therapeutically effective amount can also be an amount which is prophylactically effective. The amount which is therapeutically effective depends on the patient's gender and size, the condition to be treated, the condition's severity, and the result sought. For a given patient, a therapeutically effective amount can be determined by methods known to those in the art.

The term "patient" refers to an animal, including but not limited to a mammal, a primate (e.g., a human), cow, pig, sheep, goat, horse, dog, cat, rabbit, rat, or mouse.

The term "cancer" or "neoplastic disorder" refers to a tumor resulting from abnormal or uncontrolled cellular growth. Examples of cancers include but are not limited to breast cancers, colon cancers, colorectal cancers, prostate cancers, ovarian cancers, pancreatic cancers, lung cancers, gastric cancers, esophageal cancers, glioma cancers, and hematologic malignancies. Examples of neoplastic disorders include but are not limited to hematopoietic disorders, such as the myeloproliferative disorders, essential thrombocytosis, thrombocythemia, angiogenic myeloid metaplasia, polycythemia vera, myelofibrosis, myelofibrosis with myeloid metaplasia, chronic idiopathic myelofibrosis, the cytopenias, and pre-malignant myelodysplastic syndromes.

The term "hematologic malignancy" refers to cancer of the bone marrow and lymphatic tissue—body's blood-forming and immune system. Examples of hematological malignancies include but are not limited to myelodysplasia, lymphomas, leukemias, lymphomas (non-Hodgkin's lymphoma), Hodgkin's disease (also known as Hodgkin's lymphoma), and myeloma, such as acute lymphocytic leukemia (ALL), adult T-cell ALL, acute myeloid leukemia (AML), AML with trilineage myelodysplasia, acute promyelocytic leukemia, acute undifferentiated leukemia, anaplastic large-cell lymphoma, chronic lymphocytic leukemia, chronic myeloid leukemia, chronic neutrophilic leukemia, juvenile myelomonocyctic leukemia, mixed lineage leukemia, myeloproliferative disorders, myelodysplastic syndromes, multiple myeloma, and prolymphocytic leukemia.

The term "leukemia" refers to malignant neoplasms of the blood-forming tissues including but not limited to acute lymphoblastic leukemia, acute myeloid leukemia, acute myeloblastic leukemia, chronic lymphocytic leukemia, and chronic myelocytic leukemia. The leukemia can be relapsed, refractory, or resistant to conventional therapy.

The term "neurodegenerative disorder" refers to a disorder in which progressive loss of neurons occurs either in the peripheral nervous system or in the central nervous system. Examples of neurodegenerative disorders include but are not limited to chronic neurodegenerative diseases such as diabetic peripheral neuropathy, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis ("ALS"), degenerative ataxias, cortical basal degeneration, ALS-Parkinson's-Dementia complex of Guam, subacute sclerosing panencephalitis, Huntington's disease, Parkinson's disease, multiple sclerosis, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Wernicke-Korsakoff's related dementia (alcohol induced dementia), Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia). Other conditions also included within the methods of the present disclosure include age-related dementia and other dementias, and conditions with memory loss including vascular dementia, diffuse white matter disease (Binswanger's disease), dementia of endocrine or metabolic origin, dementia of head trauma and diffuse brain damage, dementia pugilistica, and frontal lobe dementia. Also other neurodegenerative disorders resulting from cerebral ischemia or infarction including embolic occlusion and thrombotic occlusion as well as intracranial hemorrhage of any type (including but not limited to epidural, subdural, subarachnoid, and intracerebral), and intracranial and intravertebral lesions (including but not limited to contusion, penetration, shear, compression, and laceration). Thus, the term "neurodegenerative disorder" also encompasses acute neurodegenerative disorders such as those involving stroke, traumatic brain injury, schizophrenia, peripheral nerve damage, hypoglycemia, spinal cord injury, epilepsy, anoxia, and hypoxia.

In certain embodiments, the neurodegenerative disorder is selected from Alzheimer's disease, Parkinson's disease, amyotrophic lateral sclerosis, age-related memory loss, senility, and age-related dementia. In another embodiment, the neurodegenerative disorder is Alzheimer's disease, also characterized as an amyloidosis. Thus, other embodiments of the disclosure relate to the treatment or prevention of other amyloidosis disorders which share features, includin, but not limited to, hereditary cerebral angiopathy, normeuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, Finnish amyloidosis, and Iowa amyloidosis.

The term "pharmaceutically acceptable carrier" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or an organ of a patient without excessive toxicity, irritation, allergic response, immunogenicity, or other problems or complications, commensurate with a reasonable benefit/risk ratio. Pharmaceutically acceptable carriers are known in the art; see, e.g., *Pharmaceutical Preformulation and Formulation* (Gibson, ed., $2^{nd}$ Ed., CRC Press, Boca Raton, Fla., 2009); *Handbook of Pharmaceutical Additives* (Ash and Ash, eds., $3^{rd}$ Ed., Gower Publishing Co., Aldershot, UK, 2007); *Remington's Pharmaceutical Sciences* (Gennaro, ed., $19^{th}$ Ed., Mack Publishing, Easton, Pa., 1995); and *Handbook of Pharmaceutical Excipients* (Amer. Pharmaceutical Ass'n, Washington, D.C., 1986).

In another embodiment, a pharmaceutical composition is formed from a Compound of Formula (1) and a pharmaceutically acceptable carrier by a method known in the art. Thus, another embodiment relates to a pharmaceutical composition comprising a Compound of Formula (1) and a pharmaceutically acceptable carrier. Such a composition is useful for treating or preventing cancer or a neurodegenerative disorder, e.g., in a patient in need thereof.

Another embodiment relates to a method for treating or preventing cancer or a neurodegenerative disorder, comprising administering to a patient in need thereof a therapeutically effective amount of a Compound of Formula (1). Another embodiment relates to a method for treating or preventing cancer or a neurodegenerative disorder, comprising administering to a patient in need thereof a therapeutically effective amount of a pharmaceutical composition comprising a Compound of Formula (1). Another embodiment relates to a method for treating cancer or a neurodegenerative disorder, comprising administering to a patient in need thereof a therapeutically effective amount of a Compound of Formula (1). Another embodiment relates to a method for treating cancer or a neurodegenerative disorder, comprising administering to a patient in need thereof a therapeutically effective amount of a pharmaceutical composition comprising a Compound of Formula (1). Another embodiment relates to a method for preventing cancer or a neurodegenerative disorder, comprising administering to a patient in need thereof a therapeutically effective amount of a Compound of Formula (1). Another embodiment relates to a method for preventing cancer or a neurodegenerative disorder, comprising administering to a patient in need thereof a therapeutically effective amount of a pharmaceutical composition comprising a Compound of Formula (1). Another embodiment relates to the use of a Compound of Formula (1) in the manufacture of a medicament useful for treating cancer or a neurodegenerative disorder or for preventing cancer or a neurodegenerative disorder.

Another embodiment relates to a method for the inhibition of Hsp90, comprising contacting Hsp90 with an Hsp90 function inhibiting amount of a Compound of Formula (1). An exemplary determination of an Hsp90 function inhibiting amount is provided in the example below entitled "Hsp90 Binding Assay." In one embodiment, the $IC_{50}$ determined by the "Hsp90 Binding Assay" provided herein is less than 10 µM. In another embodiment, the $IC_{50}$ determined by the "Hsp90 Binding Assay" provided herein is less than 1 µM. In another embodiment, the $IC_{50}$ determined by the "Hsp90 Binding Assay" provided herein is ≤0.1 µM. Another embodiment relates to the use of a Compound of Formula (1) in formulating a pharmaceutical composition for the inhibition of Hsp90.

The following examples are set forth to assist in understanding the invention and should not be construed as specifically limiting the invention as described and claimed herein. Variations of the invention, including the substitution of all equivalents now known or later developed, that would be within the purview of those in the art, and changes in formulation or changes in experimental design, are to be considered to fall within the scope of the invention incorporated herein.

4. EXAMPLES

Certain examples below relate to the synthesis of illustrative compounds of the disclosure.

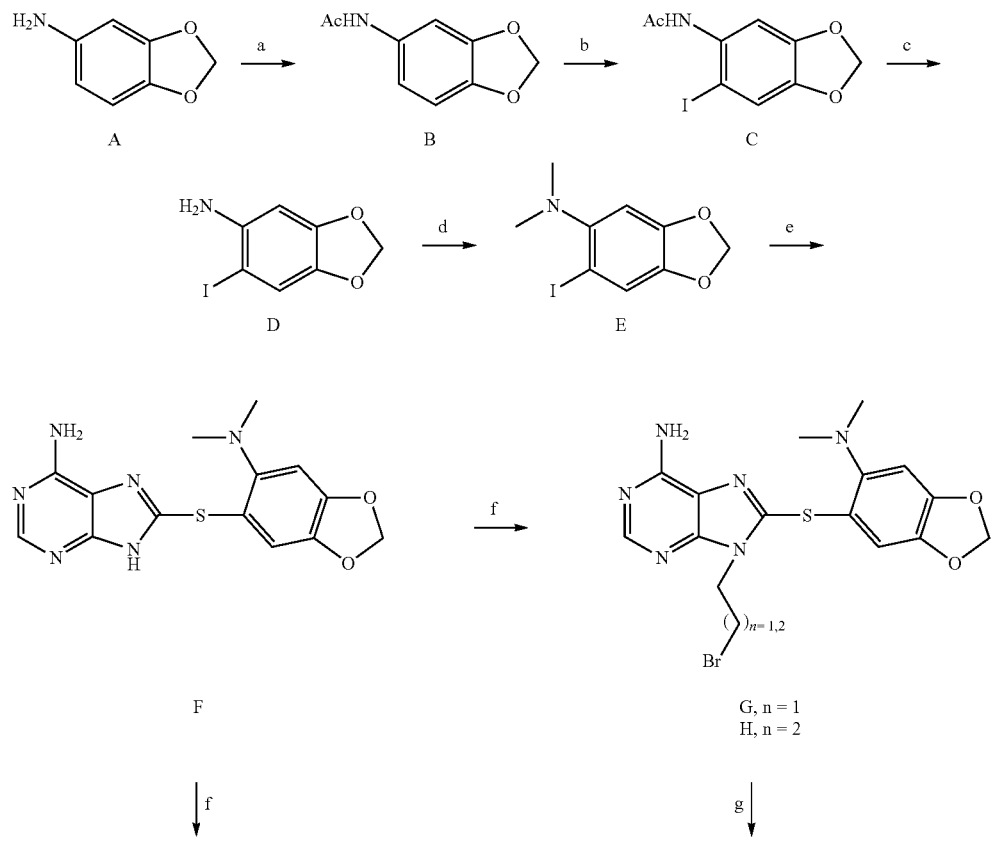

Scheme 1. Synthesis of DZ4-132, DZ4-134, DZ4-135, and Related Compounds

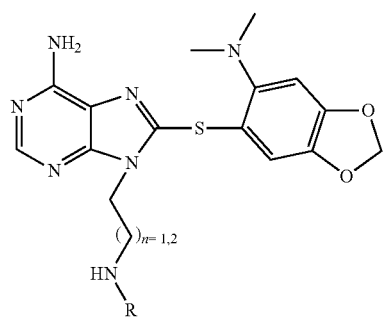
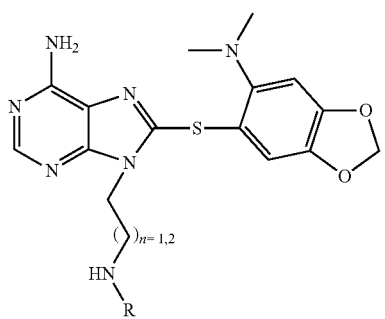

R = methanesulfonyl,
t-butylsulfonyl,
i-propylsulfonyl,
acetyl,
t-butylcarbonyl, etc n = 1, R = neopentyl, DZ4-132
n = 2, R = i-propyl, DZ4-134
n = 2, R = t-butyl, DZ4-135

Reagents and conditions: (a) Ac$_2$O, AcOH, rt; (b) ICl, CH$_2$Cl$_2$, AcOH, rt; (c) NaOH, EtOH, H$_2$O, reflux; (d) paraformaldehyde, NaBH$_3$CN, MeOH, 50° C.; (e) 8-mercaptoadenine, neocuproine, CuI, NaOtBu, DMF, 115° C.; (f) 1,2-dibromoethane/1,3-dibromopropane or corresponding bromides, Cs$_2$CO$_3$, DMF, rt; (g) amines, DMF, rt N-(benzo[d][1,3]dioxol-5-yl)acetamide (B)

To a solution of 3,4-(methylenedioxy)aniline (5.0 g, 36 5 mmol) in AcOH (75 mL) was added acetic anhydride (30 mL). The reaction mixture was stirred at a temperature of about 25° C. for about 16 hours, then poured into a saturated NaHCO$_3$ solution and filtered. The filtrate was extracted with ethyl acetate to provide B in quantitative yield which was used without further purification.

$^1$H NMR (500 MHz, DMSO-d$_6$, δ): 9.82 (s, 1H), 7.29 (d, J=1.4 Hz, 1H), 6.93 (dd, J=8.3, 1.4 Hz, 1H), 6.83 (d, J=8.3 Hz, 1H), 5.97 (s, 2H), 1.99 (s, 3H).

MS (ESI): m/z=180.1 [M+H]$^+$.

N-(6-iodobenzo[d][1,3]dioxol-5-yl)acetamide (C)

A 1.0 M solution of iodine monochloride in methylene chloride (46.5 mL) was added dropwise to a solution of B (6.4 g, 35.8 mmol) in methylene chloride (42 mL) and acetic acid (7 mL). The reaction mixture was stirred for about 16 hours then washed with saturated sodium thiosulfate and brine. The methylene chloride solution was dried over MgSO$_4$, filtered and concentrated under reduced pressure to provide a residue which was purified by chromatography (CH$_2$Cl$_2$:EtOAc, 20:1) to provide C (6.0 g, 55% yield).

$^1$H NMR (500 MHz, DMSO-d$_6$, δ): 9.33 (s, 1H), 7.37 (s, 1H), 6.96 (s, 1H), 6.07 (s, 2H), 2.01 (s, 3H).

MS (ESI): m/z=328.0 [M+Na]$^+$.

6-Iodobenzo[d][1,3]dioxol-5-amine (D)

A solution of C (3.2 g, 10 5 mmol) and NaOH (21 g, 525 mmol) in ethanol (420 mL) and water (96 mL) was refluxed for 4 h. The reaction mixture was cooled and concentrated under reduced pressure to provide a residue that was partitioned between methylene chloride and water. The organic layer was washed with water, dried over MgSO$_4$, filtered and concentrated under reduced pressure to provide a residue which was purified by chromatography (hexane:CH$_2$Cl$_2$, 7:3) to provide D (2.1 g, 76% yield).

$^1$H NMR (500 MHz, CDCl$_3$, δ): 7.05 (s, 1H), 6.38 (s, 1H), 5.87 (s, 2H), 3.85 (br s, 2H).

MS (ESI): m/z=264.0 [M+H]$^+$.

6-Iodo-N,N-dimethylbenzo[d][1,3]dioxol-5-amine (E)

To a mixture of D (200 mg, 0.7604 mmol), paraformaldehyde (228 mg, 7.604 mmol), and molecular sieves (2 g) in methylene chloride (4 ml) and AcOH (0.435 mL, 7.604 mmol) was added NaBH$_3$CN. The mixture was heated to 50° C. for 2 h. To the reaction mixture was added water and the organic layer was separated and the aqueous layer was further extracted with methylene chloride a few times. The organic layers were combined and washed with brine, dried over MgSO$_4$, filtered and concentrated under reduced pressure to provide E (181 mg, 82% yield) which was used without further purification.

$^1$H NMR (500 MHz, CDCl$_3$, δ): 7.25 (s, 1H), 6.74 (s, 1H), 5.95 (s, 2H), 2.65 (s, 6H).

MS (ESI): m/z=292.1 [M+H]$^+$.

8-(6-(Dimethylamino)benzo[d][1,3]dioxol-5-ylthio)-9H-purin-6-amine (F)

A mixture of 8-mercaptoadenine (160 mg, 0.978 mmol), neocuproine hydrate (40.7 mg, 0.196 mmol), CuI (36.4 mg, 0.196 mmol), sodium tert-butoxide (0.184 mg, 1.91 mmol), E (370 mg, 1.27 mmol) and DMF (4 mL) were heated at 115° C. for 32 h. The solvent was removed under reduced pressure and the residue was purified by preparatory TLC (CH$_2$Cl$_2$:MeOH—NH$_3$ (7N), 10:1) to provide F (123 mg, 39% yield).

$^1$H NMR (500 MHz, CDCl$_3$/MeOH-d$_4$, δ): 8.15 (s, 1H), 6.86 (s, 1H), 6.81 (s, 1H), 5.97 (s, 2H), 2.72 (s, 6H).

MS (ESI): m/z=331.3 [M+H]$^+$.

9-(2-Bromoethyl)-8-(6-(dimethylamino)benzo[d][1,3]dioxol-5-ylthio)-9H-purin-6-amine (G)

F (29 mg, 0.0878 mmol), Cs$_2$CO$_3$ (42.9 mg, 0.1317 mmol), 1,2-dibromoethane (82.5 mg, 37.8 µL, 0.439 mmol) in DMF (0.6 mL) was stirred for 1.5 h at a temperature of about 25° C. Then additional Cs$_2$CO$_3$ (14 mg, 0.043 mmol) was added and the mixture stirred for an additional 20 min.

The mixture was dried under reduced pressure and the residue purified by preparatory TLC (CH$_2$Cl$_2$:MeOH:AcOH, 15:1:0.5) to provide G (24 mg, 63% yield).

$^1$H NMR (500 MHz, CDCl$_3$/MeOH-d$_4$, δ): 8.24 (s, 1H), 6.81 (s, 1H), 6.68 (s, 1H), 5.96 (s, 2H), 4.62 (t, J=6.9 Hz, 2H), 3.68 (t, J=6.9 Hz, 2H), 2.70 (s, 6H).

MS (ESI): m/z=437.2/439.1 [M+H]$^+$.

8-(6-(Dimethylamino)benzo[d][1,3]dioxol-5-ylthio)-9-(2-(neopentylamino)ethyl)-9H-purin-6-amine (DZ4-132)

G (24 mg, 0.0549 mmol) and neopentylamine (239 mg, 2.7 mmol) in DMF (0.50 mL) was stirred at a temperature of about 25° C. for about 16 hours. Solvent was removed under reduced pressure and the resulting residue was purified by preparatory TLC (CH$_2$Cl$_2$:MeOH—NH$_3$ (7N), 20:1) to provide 20.6 mg (85% yield) of DZ4-132.

$^1$H NMR (500 MHz, CDCl$_3$/MeOH-d$_4$, δ): 8.16 (s, 1H), 6.73 (s, 1H), 6.55 (s, 1H), 5.88 (s, 2H), 4.27 (t, J=6.4 Hz, 2H), 2.91 (t, J=6.4 Hz, 2H), 2.61 (s, 6H), 2.28 (s, 2H), 0.79 (s, 9H).

$^{13}$C NMR (125 MHz, CDCl$_3$/MeOH-d$_4$, δ): 154.8, 152.9, 151.8, 149.4, 149.2, 148.7, 145.2, 120.0, 118.7, 111.6, 102.9, 102.3, 62.4, 50.1, 45.7, 44.1, 31.9, 28.1.

MS (ESI): m/z=444.3 [M+H]$^+$.

9-(3-Bromopropyl)-8-(6-(dimethylamino)benzo[d][1,3]dioxol-5-ylthio)-9H-purin-6-amine (H)

F (60 mg, 0.1818 mmol), Cs$_2$CO$_3$ (88.8 mg, 0.2727 mmol), 1,3-dibromopropane (184 mg, 93 μL, 0.909 mmol) in DMF (2 mL) was stirred for 40 min. at a temperature of about 25° C. The mixture was dried under reduced pressure and the residue purified by preparatory TLC (CH$_2$Cl$_2$:MeOH:AcOH, 15:1:0.5) to provide H (60 mg, 73% yield).

$^1$H NMR (500 MHz, CDCl$_3$, δ): 8.26 (s, 1H), 6.84 (br s, 2H), 6.77 (s, 1H), 6.50 (s, 1H), 5.92 (s, 2H), 4.35 (t, J=7.0 Hz, 2H), 3.37 (t, J=6.6 Hz, 2H), 2.68 (s, 6H), 2.34 (m, 2H).

MS (ESI): m/z=451.1/453.1 [M+H]$^+$.

8-(6-(Dimethylamino)benzo[d][1,3]dioxol-5-ylthio)-9-(3-(isopropylamino)propyl)-9H-purin-6-amine (DZ4-134)

H (30 mg, 0.0665 mmol) and isopropylamine (196 mg, 283 μL, 3.3 mmol) in DMF (1 mL) was stirred at a temperature of about 25° C. for about 16 hours. Solvent was removed under reduced pressure and the resulting residue was purified by preparatory TLC (CH$_2$Cl$_2$:MeOH—NH$_3$ (7N), 20:1) to provide 21.8 mg (78% yield) of DZ4-134.

$^1$H NMR (500 MHz, CDCl$_3$, δ): 8.24 (s, 1H), 6.69 (s, 1H), 6.39 (s, 1H), 5.98 (br s, 2H), 5.83 (s, 2H), 4.23 (t, J=6.9 Hz, 2H), 2.68 (septet, J=6.3 Hz, 1H), 2.61 (s, 6H), 2.48 (t, J=6.8 Hz, 2H), 1.95 (m, 2H), 0.99 (d, J=6.3 Hz, 6H).

$^{13}$C NMR (125 MHz, CDCl$_3$, δ): 155.3, 153.6, 152.3, 148.7, 147.7, 147.0, 145.4, 121.1, 120.8, 109.7, 103.1, 102.3, 49.6, 45.9, 44.2, 42.1, 30.5, 23.1.

MS (ESI): m/z=430.2 [M+H]$^+$.

9-(3-(tent-Butylamino)propyl)-8-(6-(dimethylamino)benzo[d][1,3]dioxol-5-ylthio)-9H-purin-6-amine (DZ4-135)

H (30 mg, 0.0665 mmol) and tert-butylamine (243 mg, 350 μL, 3.3 mmol) in DMF (1 mL) was stirred at a temperature of about 25° C. for about 16 hours. Solvent was removed under reduced pressure and the resulting residue was purified by preparatory TLC (CH$_2$Cl$_2$:MeOH—NH$_3$ (7N), 20:1) to provide 18.5 mg (63% yield) of DZ4-135.

$^1$H NMR (500 MHz, CDCl$_3$, δ): 8.25 (s, 1H), 6.69 (s, 1H), 6.40 (s, 1H), 5.88 (br s, 2H), 5.83 (s, 2H), 4.23 (t, J=7.0 Hz, 2H), 2.62 (s, 6H), 2.43 (t, J=6.8 Hz, 2H), 1.91 (m, 2H), 0.98 (s, 9H).

MS (ESI): m/z=444.2 [M+H]$^+$.

Hsp90 Binding Assay:

For the binding studies, fluorescence polarization (FP) assays were performed similarly as was previously reported [Du et al. (2007) "High-throughput screening fluorescence polarization assay for tumor-specific Hsp90" J. Biomol. Screen 12:915-924]. Briefly, FP measurements were performed on an Analyst GT instrument (Molecular Devices, Sunnyvale, Calif.). Measurements were taken in black 96-well microtiter plates (Corning # 3650) where both the excitation and the emission occurred from the top of the well. A stock of 10 μM cy3B-GM was prepared in DMSO and diluted with HFB buffer (20 mM Hepes (K), pH 7.3, 50 mM KCl, 2 mM DTT, 5 mM MgCl$_2$, 20 mM Na$_2$MoO$_4$, and 0.01% NP40 with 0.1 mg/mL BGG). The test compounds were dissolved in DMSO and added at several concentrations to the HFB assay buffer containing both 6 nM cy3B-GM and transgenic mouse brain lysate (6 μg JNPL3 lysate) or human cancer cell lysate (3 μg SKBr3 lysate) in a final volume of 100 μL. Drugs were added to triplicate wells. Free cy3B-GM (6 nM cy3B-GM), bound cy3B-GM (6 nM cy3B-GM+lysate, as indicated above) and buffer only containing wells (background) were included as controls in each plate. Plates were incubated on a shaker at 4° C., and polarization values measured at 24 h. Percentage inhibition was calculated as follows: (% Control)=100−((mP$_c$−mP$_f$)/(mP$_b$−mP$_f$))×100, where mP$_c$ is the recorded mP from compound wells, mP$_f$ is the average recorded mP from cy3B-GM-only wells, and mP$_b$ is the average recorded mP from wells containing both cy3B-GM and lysate, and plotted against values of competitor concentrations. The inhibitor concentration at which 50% of bound cy3B-GM was displaced was obtained by fitting the data using a nonlinear regression analysis as implemented in Prism 4.0 (GraphPad Software).

In these assays, the following simplified Hsp90 binding grading was used: I≥10 μM; 10 μM>II>1 μM; 1 μM>III>0.1 μM; IV≤0.1 μM for C$_{50}$. As shown, each of the compounds tested showed an IC$_{50}$ of less than or equal to 0.1 μM which is a high level of activity.

Table 1 shows results of testing for Compounds DZ4-132, DZ4-134, and DZ4-135, and a comparison compound (PU-H71) of the formula

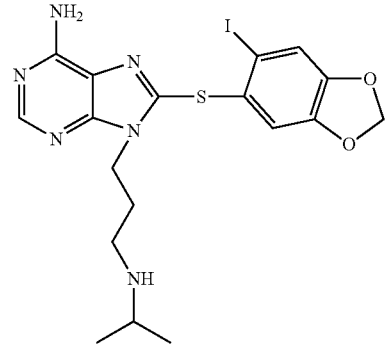 [SMILES: CC(C)NCCCn1c(Sc2cc3c(cc2I)OCO3)nc2c(N)ncnc21]

In interpreting these test results, it will be appreciated that binding to Hsp90 for activity in the treatment of cancer or neurodegenerative disorders is desirable. In contrast, it is generally undersirable to have binding to hERG since binding to hERG can result in undesirable cardiac side effects. Therefore, having a low value for binding to Hsp90 and a high value for binding to hERG is desirable, bearing in mind that the units for the two measurement are different.

TABLE 1

| Compound | SKBr3 Binding Affinity (nM) | hERG binding (uM) |
|---|---|---|
| DZ4-132 | 10.0 | 5.5 |
| DZ4-134 | 55.3 | 11.0 |
| DZ4-135 | 45.4 | 14.0 |
| PU-H71 | 20 | 1 |

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those in the art and are intended to fall within the scope of the appended claims. A number of references have been cited, the entire disclosures of which are incorporated herein by reference for all purposes.

What is claimed:

1. A compound of Formula (1):

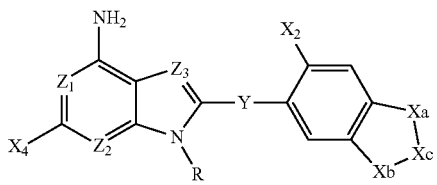

(1)

or a pharmaceutically acceptable salt thereof, wherein:
(a) each of $Z_1$, $Z_2$ and $Z_3$ is independently CH or N;
(b) Y is S;
(c) Xa and Xb are O;
(d) Xc is —$CH_2$—;
(e) $X_2$ is —$NR_1R_2$, wherein $R_1$ and $R_2$ are each independently H, $C_{1-6}$ alkyl, $C_2$-$C_6$ alkenyl, $C_{2-6}$ alkenyl, cycloalkyl, heteroalkyl, heterocycloalkyl, aryl, heteroaryl, alkylaryl, arylalkyl, alkylheteroaryl, heteroarylalkyl, or alkylheteroarylalkyl;
(f) $X_4$ is hydrogen or halogen;
(g) R is —$R_{10}$—NH—$R_{11}$ wherein $R_{10}$ is ethylene or propylene, and
  (i) $R_{11}$ is isopropyl or t-butyl, or
  (ii) $R_{11}$ is a branched alkyl, $Z_1$, $Z_2$ and $Z_3$ are each N, and $R_1$ and $R_2$ are each independently alkyl which has 1, 3, 4, 5, or 6 carbon atoms, $C_2$-$C_6$ alkenyl, $C_{2-6}$ alkynyl, cycloalkyl, heteroalkyl, heterocycloalkyl, aryl, heteroaryl, alkylaryl, arylalkyl, alkylheteroaryl, heteroarylalkyl, or alkylheteroarylalkyl.

2. The compound of claim 1, or a pharmaceutically acceptable salt thereof, wherein $X_2$ is dimethylamine.

3. The compound of claim 1, or a pharmaceutically acceptable salt thereof, wherein $R_{11}$ is neopentyl.

4. The compound of claim 1 or 2, or a pharmaceutically acceptable salt thereof, wherein $R_{11}$ is isopropyl.

5. The compound of claim 1 or 2, or a pharmaceutically acceptable salt thereof, wherein $R_{11}$ is t-butyl.

6. The compound of any of claims 1 or a pharmaceutically acceptable salt thereof, wherein $Z_1$, $Z_2$ and $Z_3$ are each N.

7. The compound of claim 1, or a pharmaceutically acceptable salt thereof, wherein $Z_1$, $Z_2$ and $Z_3$ are each N, $X_2$ is dimethylamine, Y is S, $R_{10}$ is ethylene, $R_{11}$ is neopentyl, and X, is H.

8. The compound of claim 1 or a pharmaceutically acceptable salt thereof, wherein $Z_1$, $Z_2$ and $Z_3$ are each N, $X_2$ is dimethlyamine, Y is S, $R_{10}$ is propylene, $R_{11}$ is isopropyl, and $X_4$ is H.

9. The compound of claim 1 or a pharmaceutically acceptable salt thereof, wherein $Z_1$, $Z_2$ and $Z_3$ are each N, $X_2$ is dimethlyamine, Y is S, $R_{10}$ is propylene, $R_{11}$ is t-butyl, and $X_4$ is H.

10. A pharmaceutical composition comprising the compound of claim 1, or a pharmaceutically acceptable salt thereof, and a pharmaceutically acceptable carrier.

11. A method for the inhibition of Hsp90, comprising contacting Hsp90 with an Hsp90 function inhibiting amount of a compound of claims 1.

* * * * *